United States Patent
Burger et al.

(10) Patent No.: US 10,377,689 B2
(45) Date of Patent: Aug. 13, 2019

(54) PROCESS FOR PREPARING POLYOXYMETHYLENE DIMETHYL ETHERS FROM FORMALDEHYDE AND METHANOL IN AQUEOUS SOLUTIONS

(71) Applicant: OME Technologies GmbH, Kaiserslautern (DE)

(72) Inventors: Jakob Burger, Kaiserslautern (DE); Niklas Schmitz, Kaiserslautern (DE); Hans Hasse, Kaiserslautern (DE); Eckhard Stroefer, Mannheim (DE)

(73) Assignee: OME TECHNOLOGIES GMBH, Kaiserslautern (DE)

( * ) Notice: Subject to any disclaimer, the term of this patent is extended or adjusted under 35 U.S.C. 154(b) by 0 days.

(21) Appl. No.: 15/807,092

(22) Filed: Nov. 8, 2017

(65) Prior Publication Data
US 2018/0134642 A1 May 17, 2018

(30) Foreign Application Priority Data

Nov. 17, 2016 (DE) .......... 10 2016 222 657
Jul. 28, 2017 (DE) .......... 10 2017 213 062

(51) Int. Cl.
*C07C 41/56* (2006.01)
*C07C 41/58* (2006.01)
(Continued)

(52) U.S. Cl.
CPC .............. *C07C 41/56* (2013.01); *B01D 3/009* (2013.01); *B01D 3/143* (2013.01); *C07C 41/48* (2013.01);
(Continued)

(58) Field of Classification Search
None
See application file for complete search history.

(56) References Cited

U.S. PATENT DOCUMENTS

| 2,449,469 A | 9/1948 | Gresham et al. |
| 5,746,785 A | 5/1998 | Moulton et al. |

(Continued)

FOREIGN PATENT DOCUMENTS

| EP | 1074296 A1 | 2/2001 |
| EP | 2987781 A1 | 2/2016 |
| WO | WO 2006/045506 A1 | 5/2006 |

OTHER PUBLICATIONS

Baerns et al., "Technische Chemie," Table on Contents, Wiley-VCH, Weinheim, 2006, pp. V-XII.
(Continued)

*Primary Examiner* — Rosalynd A Keys
(74) *Attorney, Agent, or Firm* — Birch, Stewart, Kolasch & Birch LLP (57) ABSTRACT

Process for preparing polyoxymethylene dimethyl ethers having ≥3 oxymethylene units ($OME_{n\geq3}$), comprising the steps:
(i) introduction of formaldehyde, methanol and water into a reactor R and reaction to give a reaction mixture containing formaldehyde, water, methylene glycol, polyoxymethylene glycols, methanol, hemiformals, methylal ($OME_{n=1}$) and polyoxymethylene dimethyl ethers ($OME_{n>1}$);
(ii) introduction of the reaction mixture into a reactive distillation column K1 and separation into a low boiler fraction F1 containing formaldehyde, water, methylene glycol, polyoxymethylene glycols, methanol, hemiformals, methylal ($OME_{n=1}$) and polyoxymethylene dimethyl ethers having from 2 to 3 oxymethylene units ($OME_{n=2-3}$) and a high boiler fraction F2 containing polyoxymethylene dimethyl ethers having more than two oxymethylene units ($OME_{n\geq3}$).

15 Claims, 1 Drawing Sheet

(51) Int. Cl.
*C07C 41/60* (2006.01)
*B01D 3/00* (2006.01)
*B01D 3/14* (2006.01)
*C07C 41/48* (2006.01)
*C07C 43/11* (2006.01)

(52) U.S. Cl.
CPC .............. *C07C 41/58* (2013.01); *C07C 41/60* (2013.01); *C07C 43/11* (2013.01); *Y02P 20/127* (2015.11)

(56) References Cited

U.S. PATENT DOCUMENTS

| | | | |
|---|---|---|---|
| 5,914,012 A | 6/1999 | Kaibel et al. | |
| 6,392,102 B1 | 5/2002 | Hagen et al. | |
| 6,427,985 B1 | 8/2002 | Kaibel et al. | |
| 6,534,685 B1 | 3/2003 | Patrini et al. | |
| 6,610,888 B1 | 8/2003 | Ströfer et al. | |
| 7,193,115 B2 | 3/2007 | Ströfer et al. | |
| 7,273,955 B2 | 9/2007 | Stroefer et al. | |
| 7,342,139 B2 | 3/2008 | Rumpf et al. | |
| 7,345,207 B2 | 3/2008 | Stroefer et al. | |
| 7,390,932 B2 | 6/2008 | Stroefer et al. | |
| 7,414,159 B2 | 8/2008 | Stroefer et al. | |
| 7,671,240 B2 | 3/2010 | Stroefer et al. | |
| 7,700,809 B2 * | 4/2010 | Stroefer | C08G 16/0212 568/618 |
| 7,999,140 B2 | 8/2011 | Stroefer et al. | |
| 2007/0260094 A1 | 11/2007 | Schelling et al. | |
| 2011/0313202 A1 | 12/2011 | Xia et al. | |
| 2014/0114093 A1 | 4/2014 | Chen et al. | |
| 2015/0053616 A1 | 2/2015 | Himeno et al. | |
| 2015/0094497 A1 | 4/2015 | Chen et al. | |

OTHER PUBLICATIONS

Burger et al., "Production Process for Diesel Fuel Components Poly(oxymethylene) Dimethyl Ethers from Methane-based Products by Hierarchical Optimization with Varying Model Depth," Chemical Engineering Research and Design, vol. 91, No. 12, 2013, pp. 2648-2662.

Devaux et al., "Electro-oxidation of Hydrolysed Poly-oxymethylene-dimethylether on PtRu Supported Catalysts," Electrochimica Acta, vol. 56, No. 3, 2011 (Available online Nov. 10, 2010), pp. 1460-1465.

Frolkova et al., "Bioethanol Dehydration: State of the Art," Theoretical Foundations of Chemical Engineering, vol. 44, No. 4, 2010, pp. 545-556 (published in Khimicheskaya Tekhnologiya, 2009, vol. 10, No. 8, pp. 469-482.

Hahnenstein et al., "NMR Spectroscopic and Densimetric Study of Reaction Kinetics of Formaldehyde Polymer Formation in Water, Deuterium Oxide, and Methanol," Industrial and Engineering Chemistry Research, vol. 34, No. 2, 1995, pp. 440-450.

Hasse, "Vapor-liquid Equilibria, Enthalpies, and Reaction Kinetics in Formaldehyde Containing Mixtures," Ph.D. Thesis, University of Kaiserslautern, 1990, pp. III, V-VIII (Total 7 pages), with English summary.

Masamoto et al., "Development of Methylal Synthesis by Reactive Distillation," Journal of Chemical Engineering of Japan, vol. 27, No. 1, 1994, pp. 1-5.

Melin et al., "Membrane Processes," Table of Contents with English translation, Springer-Verlag, 2007, 14 pages.

Olah et al., "Beyond Oil and Gas: The Methanol Economy," Second Updated and Enlarged Edition, Table of Contents, Wiley-VCH, 2011, pp. V-IX.

Reuss et al., "Encyclopedia of Industrial Chemistry," vol. A 11, Wiley-VCH, Weinheim, 1988, pp. 619-651.

Schmitz et al., "Chemical Equilibrium of the Synthesis of Poly(oxymethylene) Dimethyl Ethers from Formaldehyde and Methanol in Aqueous Solutions," Industrial and Engineering Chemistry Research, vol. 54, No. 25, 2015 (Published Jun. 2, 2015), pp. 6409-6417.

Schmitz et al., "From Methanol to the Oxygenated Diesel Fuel Poly(oxymethylene) Dimethyl Ether: An Assessment of the Production Costs," Fuel, vol. 185, 2016, pp. 67-72.

Schmitz et al., "Liquid-liquid Equilibrium in Binary and Ternary Mixtures Containing Formaldehyde, Water, Methanol, Methylal, and Poly(oxymethylene) Dimethyl Ethers," Fluid Phase Equilibria, vol. 425, 2016, pp. 127-135.

Schmitz, "Reaction Kinetics of the Formation of Poly(oxymethylene) Dimethyl Ethers from Formaldehyde and Methanol in Aqueous Solutions," vol. 54, No. 50, 2015 (Published Dec. 4, 2015), pp. 12553-12560.

* cited by examiner

PROCESS FOR PREPARING POLYOXYMETHYLENE DIMETHYL ETHERS FROM FORMALDEHYDE AND METHANOL IN AQUEOUS SOLUTIONS

The invention relates to a process for preparing polyoxymethylene dimethyl ethers (OME) having ≥3 oxymethylene units from formaldehyde and methanol in aqueous solution.

OMEs represent a homologous series of the general formula $CH_3O(CH_2O)_nCH_3$, where n is ≥2. Like the parent molecule of the homologous series, methylal $CH_3O(CH_2O)_nCH_3$ (n=1), the OMEs are acetals. They are prepared by reaction of methanol with aqueous formaldehyde in the presence of an acid catalyst. Like other acetals, they are stable under neutral or alkaline conditions, but are attacked by acids. In the presence of water, they are converted by hydrolysis into hemiacetals and methanol in a first step. In a second step, the hemiacetals are converted into formaldehyde and methanol. In the following, polyoxymethylene dimethyl ethers having n oxymethylene units will be referred to as $OME_n$ for short.

On the laboratory scale, OMEs are prepared by heating polyoxymethylene glycol or paraformaldehyde with methanol in the presence of traces of sulfuric acid or hydrochloric acid at temperatures of from 150 to 180° C. and reaction times of from 12 to 15 hours, as described in Reuss G., Disteldorf W., Grundler O., Hilt A., Ullmanns Encyclopedia of Industrial Chemistry, Wiley-VCH, Weinheim 1988. Here, decomposition reactions with formation of carbon dioxide and formation of dimethyl ether occur. At a paraformaldehyde or polyoxymethylene glycol to methanol ratio of 6:1, polymers having n>100, generally n=300 to 500, are obtained. The products are washed with sodium sulfite solution and subsequently fractionated by crystallization. The method of laboratory preparation cannot be transferred directly to the industrial scale. The product mixture obtained is outside the bandwidth of fields of use which are of interest.

OMEs are, inter alia, of interest as diesel fuel, as absorption medium for separating carbon dioxide from gas mixtures (Burger J., Ströfer E., Hasse H. Production process for diesel fuel components poly(oxymethylene) dimethyl ethers from methane-based products by hierarchical optimization with varying model depth. Chemical Engineering Research and Design. 2013, 91(12), 2648-2662) or as safe fuels for fuel cells (Devaux D., Yano H., Uchida H., Dubois J. L., Watanabe M. Electro-oxidation of hydrolysed polyoxymethylene-dimethylether on PtRu supported catalysts Electrochimica Acta. 2011, 56(3)., 1460-1465). The use as diesel fuel is of particular interest here, since both OMEs having one chain length and also OME mixtures containing OMEs of various chain lengths lead to a reduction in particulates formation during combustion. The OMEs having one chain length and the OME mixtures can be mixed with conventional diesel fuel or else be used directly (i.e. without addition of conventional diesel fuel) as fuel. If other oxygen-containing compounds such as methanol are added, these have significant defects. Such defects are, inter alia, the lack of solubility in diesel fuel, an unsatisfactorily low cetane number and a reduced flashpoint of the preparation obtained. These defects can in principle be eliminated by means of further additives. However, this has the disadvantages that the costs of the preparation increase by the costs of the additives, storage and blending in the production of the preparation is complicated and also the additives influence the burning properties of the preparation.

There is therefore a considerable need to prepare OMEs economically and ecologically advantageously in large amounts and in high purity.

U.S. Pat. No. 2,449,469 describes a process in which methylal is heated with paraformaldehyde or a concentrated formaldehyde solution in the presence of sulfuric acid. Polyoxymethylene dimethyl ethers having from 2 to 4 oxymethylene units per molecule are obtained here. The examples relate to batch processes; a scalable industrial process is not disclosed.

U.S. Pat. No. 5,746,785 describes the preparation of crude mixtures of OMEs having a molecular weight of from 80 to 350, corresponding to from 1 to 10 oxymethylene units (n=1 to 10) by reaction of 1 part of methylal with 5 parts of $CH_2O$ in the form of paraformaldehyde in the presence of 0.1% by weight of formic acid at a temperature of from 150 to 240° C., or by reaction of 1 part of methanol with 3 parts of $CH_2O$ in the form of paraformaldehyde at a temperature of from 150 to 240° C. The crude mixtures obtained are added in amounts of from 5 to 30% by weight to a diesel fuel. Two phases are formed here, with the lighter phase being the finished, OME-containing product which is passed to the diesel pool. The use of the heavier phase is not described.

U.S. Pat. No. 6,534,685 discloses the preparation of OMEs having from 2 to 6 formaldehyde units in the molecule by reaction of methylal with paraformaldehyde in the presence of trifluorosulfonic acid. Here, OMEs having n=2 to 5 are formed with a selectivity of 94.8%, with the dimer (n=2) being obtained in a proportion of 49.6%. The OMEs obtained are added in amounts of from 4 to 11% by weight to a diesel fuel. Only the synthesis of the OMEs is described; a scalable industrial process is not disclosed.

U.S. Pat. No. 6,392,102 describes the preparation of OMEs by reaction of a feedstream containing methanol and formaldehyde, which has been obtained by oxidation of dimethyl ether, in the presence of an acid catalyst and simultaneous separation of the reaction products in a catalytic distillation column. Methylal, methanol, water and OMEs are obtained here. The process has the problem that water in the process hydrolyses OMEs under the process conditions and thus reduces the process yield.

The water is introduced into the process in two ways. The starting material formaldehyde is, in the economically preferred processes for formaldehyde production which have been implemented industrially, prepared by oxidative dehydrogenation of methanol (reaction 1). This forms water as coproduct.

$$CH_3OH+(1/2)O_2 \rightarrow CH_2O+H_2O \qquad \text{(Reaction 1)}$$

Furthermore, water is also formed in the OME synthesis from formaldehyde and methanol. In such mixtures, the formaldehyde is present virtually exclusively in chemically bound form. Formaldehyde reacts in the presence of water to form methylene glycol $HO-(CH_2O)-H$ (reaction 2) and polyoxymethylene glycols $HO-(CH_2O)_n-H$ (reaction 3)

$$CH2O+H2O \leftrightarrow HO-(CH2O)-H \qquad \text{(Reaction 2)}$$

$$HO-(CH_2O)_{n-1}-H+CH_2O \leftrightarrow HO-(CH_2O)_n-H \qquad \text{(Reaction 3)}.$$

Formaldehyde reacts according to an analogous scheme with methanol to form the hemiacetals hemiformal $OH-(CH_2O)-CH_3$ (reaction 4) and polyoxymethylene hemiformals $HO-(CH_2O)_nCH_3$ (reaction 5).

$$CH_2O+CH_3OH \leftrightarrow OH-(CH_2O)-CH_3 \qquad \text{(Reaction 4)}$$

$$OH-(CH_2O)_{n-1}-CH_3+CH_2O \leftrightarrow OH-(CH_2O)_n-CH_3 \qquad \text{(Reaction 5)}$$

The unstable hemiacetals are also formed in the hydrolysis of OMEs. These hemiacetals reduce the flashpoint of the diesel fuel mixture and thus adversely affect its quality. A flashpoint of the diesel fuel mixture which is too low leads to the specifications prescribed, for example, by relevant DIN standards no longer being satisfied. Hemiacetals are, however, difficult to separate from the OMEs because of comparable boiling points. Since the reactions 2 to 4 are reversible and proceed without addition of a catalyst, the hemiacetals can potentially liberate formaldehyde again, and this is undesirable in the fuel.

In the process described in U.S. Pat. No. 6,392,102, the preparation of formaldehyde is integrated into the OME synthesis in such a way that formaldehyde is not obtained by oxidative dehydrogenation of methanol, which generally gives aqueous formaldehyde solutions having a formaldehyde content of from 20 to 60% by weight, but instead by oxidative dehydrogenation of dimethyl ether (reaction 6).

$$CH_3OCH_3 + O_2 \rightarrow 2CH_2O + H_2O \quad \text{(Reaction 6)}$$

Formaldehyde contents of >60% by weight are achieved here, since dimethyl ether is formally obtained by dehydration of two methanol molecules (reaction 7) and part of the water can be separated off as early as in the preparation of dimethyl ether.

$$2CH_3OH \leftrightarrow CH_3OCH_3 + H_2O \quad \text{(Reaction 7)}$$

As an alternative, a highly concentrated aqueous formaldehyde solution can also be prepared by concentrating the aqueous solution, as described in U.S. Pat. No. 7,342,139, and using this concentrated solution. However, the principal problem associated with the process is not solved thereby.

The process of U.S. Pat. No. 6,392,102 is correspondingly technically complex and contains many recirculations. It encompasses reactive distillations, a plurality of heterogeneously catalysed reactors, distillation columns, absorption columns and a spray tower. This requires high development and capital costs and also maintenance costs in on-going operation.

The above-described problems are avoided by working in the absence of water, as described in U.S. Pat. No. 7,999,140 and WO 2006/045506. This is achieved by the use of trioxane as water-free formaldehyde-containing component which is reacted with methylal or dimethyl ether. However, the starting material trioxane is more expensive than formaldehyde since the preparation of trioxane itself starts out from formaldehyde as starting material. An additional process step is thus required.

U.S. Pat. No. 7,671,240 describes a process for preparing $OME_{n=3-5}$ by reaction of formaldehyde with methanol in aqueous solution and subsequent work-up of the reaction mixture by distillation. However, the process indicated there has the following disadvantages: $OME_{n=3-5}$ go through a total of three distillation columns and a phase separator in order to be separated from the remaining components of the reactor output. Owing to the complexity of the reactive mixture, it is extremely difficult to find an operating point in which all of the apparatuses are connected optimally. The patent document does not contain any examples which describe such an operating point.

In particular, it is shown in Schmitz N., Friebel A., von Harbou E., Burger J., Hasse H., Liquid-liquid equilibrium in binary and ternary mixtures containing formaldehyde, water, methanol, methylal, and poly(oxymethylene) dimethyl ethers, Fluid Phase Equilibria. 2016 (425), 127 to 135, that both methanol and formaldehyde have a strong dissolution mediating effect on the mixing gap between OME and water. A high outlay is therefore necessary in order to reduce the content of formaldehyde and methanol before phase separation by distillation to such an extent that the system disintegrates into two liquid phases. If this disintegration does not take place, the process is obsolete.

According to the new prior art cited, it is also shown that the isolation of OME by the organic phase of the phase separator is not quantitative. A significant proportion of the OMEs leaves the phase separator via the aqueous phase. These OMEs have to be worked up further, which increases the complexity of the overall process and adversely affects the economics.

Nevertheless, the preparation of OME from methanol and formaldehyde in aqueous solution has considerable advantages over the use of other starting materials.

Methanol has become a platform chemical which is traded on the market and is available in large quantities. Olah (Olah G. A., Goeppert A., Surya Prakash G. K. Beyond oil and gas: the methanol economy, Wiley-VCH, Weinheim 2011) has developed a scenario showing how the world energy economy can be set up afresh on the basis of synthesis gas and methanol. Synthesis gas can be produced both conventionally on the basis of fossil raw materials and also on the basis of renewable energies. In the latter case, for example, water is electrolytically dissociated using electricity generated by solar means or geothermally (reaction 8).

$$3H_2O \rightarrow 3H_2 + (3/2)O_2 \quad \text{(Reaction 8)}$$

Part of the hydrogen is converted by means of carbon dioxide into the synthetic building block carbon monoxide (reaction 9).

$$CO_2 + H_2H \leftrightarrow CO + H_2O \quad \text{(Reaction 9)}$$

Hydrogen and carbon monoxide are subsequently converted into the platform chemicals methanol (reaction 10) or dimethyl ether (reaction 7).

$$CO + 2H_2 \rightarrow CH_3OH \quad \text{(Reaction 10)}$$

Methanol is present in liquid form under normal conditions and can therefore be handled and shipped in a simple manner. Methanol can, as a platform chemical, be used widely in the chemical industry.

Methanol is also the preferred starting material for the conventional syntheses of formaldehyde, as are indicated in the specialist literature (Reuss G., Disteldorf W., Grundler O., Hilt A., Ullmanns Encyclopedia of Industrial Chemistry, Wiley-VCH, Weinheim 1988). These convert methanol under kinetic control into formaldehyde by oxidative dehydrogenation or by a two-way mechanism of oxidative dehydrogenation coupled with a nonoxidative dehydrogenation. Certain amounts of water are always inevitably formed here (see reaction 1). In addition, the reactor output from the formaldehyde reactor is usually quenched with an excess of water in absorption columns. The product is an aqueous solution of formaldehyde which in most cases is additionally stabilized with methanol.

US 2011/0313202 describes a process for preparing OME from aqueous formaldehyde solution and methanol. In the process, aqueous formaldehyde firstly reacts partially to form trioxane, with an ionic liquid being used as catalyst. The resulting mixture containing formaldehyde, trioxane and water is subsequently reacted with methanol using a second ionic liquid as catalyst to give OME. The reactor output from the second reactor is worked up by means of distillation and a phase separator. Disadvantages of the process are again the preparation of the intermediate trioxane and the use of ionic liquids as catalyst. This increases the complexity of the process. The use of ionic liquids represents an economic disadvantage because of their high prices. They have to be recycled without losses, which is generally very complicated. Furthermore, as indicated above, the optimal integration of the phase separator into the process is complex. It is also unclear whether traces and degradation products of the ionic liquid remain in the end product.

EP 2 987 781 describes a process for preparing OME from formaldehyde and methanol. The OMEs are removed from the reaction system in a two-phase system by means of an extractant. Preference is given, as in U.S. Pat. No. 5,746,785, to using diesel fuel as extractant. The removal of water from the aqueous phase of the two-phase system is carried out by means of, for example, adsorption on molecular sieves, drying by means of anhydrous salts or by a membrane process. A disadvantage of the process is the use of an additional extractant extraneous to the process, which possibly remains in traces in the OME. In addition, OMEs are, as shown in FIGS. 3 to 6 of the document, not removed quantitatively from the reaction system. As a result, the recycle streams of the process increase and the economics of the process are adversely affected.

US 2014/0114093 describes a process for preparing polyoxymethylene dialkyl ethers, in particular OMEs, in which OMEs are formed by reaction of formaldehyde and methanol, using an ionic liquid as catalyst. The reaction mixture is subsequently worked up by extraction and distillation. The removal of water is effected by evaporation of the water from the heavy catalyst-rich phase after the extraction. Disadvantages of the process are again the use of an ionic liquid as catalyst and the use of extractants extraneous to the process.

US 2015/0094497 describes a process for preparing OME from aqueous formaldehyde solution and methanol. Here, aqueous formaldehyde solution is firstly concentrated and dried by means of vacuum drying to give solid paraformaldehyde. Paraformaldehyde subsequently reacts with methanol using an ionic liquid as catalyst to give OME. The reactor output is worked up by distillation and extraction. Disadvantages of the process are the handling of the solid paraformaldehyde, the use of an extractant extraneous to the process, the use of ionic liquids as catalyst and the complexity of the overall process consisting of concentration and drying of the aqueous formaldehyde solution, chemical reaction, extraction and distillation. In principle, people in the technical field avoid solids in processes since handling is difficult and expensive.

U.S. Pat. No. 6,534,685 describes a liquid preparation composed of $OME_{n=2-5}$ and a diesel fuel mixture having a boiling range from 150° C. to 350° C. A disadvantage of this preparation is the use of OME of only one chain length or of synthetic mixtures of OMEs of different chain lengths. This firstly requires a complicated separation of the OMEs according to their chain length by distillation, without an additional use for the fuel mixture containing OME being obtained.

In the scientific literature, there are relatively recent publications on the subject of OME, among which most are concerned with optimization of the reaction system. Schmitz et al. (Schmitz N., Homberg F., Berje J., Burger J., Hasse H. Chemical equilibrium of the synthesis of poly(oxymethylene) dimethyl ethers from formaldehyde and methanol in aqueous solutions. Industrial and Engineering Chemistry Research. 2015, 54 (25). 6409-6417; Schmitz N., Burger J., Ströfer, E., Hasse, H. From methanol to the oxygenated diesel fuel poly(oxymethylene) dimethyl ether: An assessment of the production costs. Fuel. 2016 (185), 67-72 give an overview of the literature and economics. Schmitz et al. (Schmitz N., Homberg F., Berje J., Burger J., Hasse H. Chemical equilibrium of the synthesis of poly(oxymethylene) dimethyl ethers from formaldehyde and methanol in aqueous solutions. Industrial and Engineering Chemistry Research. 2015, 54 (25). 6409-6417); also examine the chemical equilibrium of the OME synthesis from aqueous formaldehyde and methanol. It is stated that the chain length distribution of the OME in the reactor output is determined by the chemical equilibrium.

The OME reactor here is dimensioned so that the chemical equilibrium is largely attained. It is broadly true here that the deviation of the concentration of each individual OME oligomer from its respective equilibrium concentration is <30%, preferably <10%, very particularly preferably <5%. However, it is likewise possible to dimension the reactor so that the chemical equilibrium is largely not attained and the oligomer distribution of the OME is kinetically controlled (Schmitz N., Burger J., Hasse H. Reaction kinetics of the formation of poly(oxymethylene) dimethyl ethers from formaldehyde and methanol in aqueous solutions. Industrial and Engineering Chemistry Research. 2015, 54 (50). 12553-12560). The oligomer distribution in the OME product is determined decisively by the way in which the reaction is carried out in the reactor. An economically optimal preparation of the $OME_{n=3-6}$ as fuel additive is characterized in that the chain length distribution of the oligomers in the range n=3 to 6 in the fuel corresponds within a deviation of <15%, preferably within <10%, very particularly preferably a deviation of <5%, to their chain length distribution in the reactor output. Subsequent separation and work-up steps cut out only OME oligomers having too low a chain length (n<3) or too great a chain length (n>6) from the OME fraction of the reactor output and recirculate them. These oligomers having too low or too high a chain length have, owing to their physical properties, an adverse effect on the specification features of OME and the preparations produced therefrom. Such negative influences are, for example, a flashpoint which is too low at short chain lengths or an excessively cold filter plugging point at excessively great chain lengths in the blend with diesel fractions. If oligomers having n<3 and/or n>6 are to remain in the product because of set-down specifications or standards, the proportion of these can be set via the sharpness of the separation and work-up steps and recirculations or by blending.

OME is therefore a "product-by-process" since the reactor predetermines the specification in respect of the oligomer distribution. The specification is ultimately fixed by the subsequent separation and work-up steps, since oligomers which are too high and too low are cut from the OME and recycled in the process.

In an analogous way, Burger et al. (Burger J., Ströfer E., Hasse H., Production process for diesel fuel components poly(oxymethylene) dimethyl ethers from methane-based products by hierarchical optimization with varying model depth. Chemical Engineering Research and Design, 2013, 91(12), 2648-2662) have found a natural oligomer distribution of the OME of $OME_3$: 0.43 g/g, $OME_4$: 0.34 g/g, $OME_5$: 0.22 g/g, $OME_6$: <0.01 g/g in a thermodynamically determined idealized overall process for the synthesis of OME from trioxane and methylal.

There is thus still a need for processes for preparing OME which start out from the commercial and inexpensive standard products formaldehyde and methanol which are readily available in large quantities in aqueous solution. In view of their importance as diesel fuel components, there is a particular need for the selective and economical preparation of OME having from 3 to 6 oxymethylene units ($OME_{n=3-6}$).

It is therefore an object of the invention to provide an improved process for preparing $OME_{n=3-6}$, which starts out from the inexpensively available starting materials formaldehyde and methanol.

The object is achieved by a process for preparing polyoxymethylene dimethyl ethers having ≥3 oxymethylene units ($OME_{n≥3}$), comprising the steps (i) and (ii):

(i) introduction of formaldehyde, methanol and water into a reactor R and reaction to give a reaction mixture containing formaldehyde, water, methylene glycol (MG), polyoxymethylene glycols ($MG_n$), methanol, hemiformals (HF), methylal ($OME_{n=1}$) and polyoxymethylene dimethyl ethers ($OME_{n>1}$);

(ii) introduction of the reaction mixture into a reactive distillation column K1 and separation into a low boiler fraction F1 containing formaldehyde, water, methylene glycol (MG), polyoxymethylene glycols ($MG_n$), methanol, hemiformals (HF), methylal ($OME_{n=1}$) and polyoxymethylene dimethyl ethers having from 2 to 3 oxymethylene units ($OME_{n=2-3}$) and a high boiler fraction F2 containing essentially polyoxymethylene dimethyl ethers having more than two oxymethylene units ($OME_{n≥3}$).

Preference is given to a process for preparing polyoxymethylene dimethyl ethers having from 3 to 6 oxymethylene units ($OME_{n=3-6}$), comprising the additional steps (iii) and (iv):

(iii) introduction of the high boiler fraction F2 into a distillation column K2 and separation into a product fraction F3 containing polyoxymethylene dimethyl ethers having from 3 to 6 oxymethylene units ($OME_{n=3-6}$) and a high boiler fraction F4 containing polyoxymethylene dimethyl ethers having more than 6 oxymethylene units ($OME_{n>6}$);

(iv) optionally recirculation of the high boiler fraction F4 into the reactor R.

The above-defined processes preferably additionally comprise the step (v), in particular the steps (v) and (vi):

(v) introduction of the low boiler fraction F1 into an apparatus for water separation and removal of water or a water-rich fraction F6, giving a low-water stream F5;

(vi) optionally recirculation of the low-water stream F5 into the reactor.

The process of the invention, which was found after intensive research, surprisingly solves the abovementioned fundamental problems occurring in an OME production process starting out from the starting materials methanol and formaldehyde in aqueous solution. Downstream of the reactor, both new and conventional separation steps are introduced and combined with one another in a skilful way so as to result in an economically and ecologically advantageous process.

Advantageous embodiments of the process are characterized in that catalysts are present only in the solid phase and can therefore be separated easily from the fluid reaction medium;

all other materials apart from the catalysts are always present only in fluid phases as gas or liquid;

the introduction of additional auxiliaries for catalysis, extraction or separation of material is dispensed with;

a specific reactive distillation column K1 in which the OMEs having a chain length of n≥3 are separated off from the reactor output is inserted downstream of the OME reactor, leaving a low boiler fraction;

the reactive distillation column K1 has a conventional construction. Either trays, ordered packing or random packing elements are used as separation-active internals;

the pressure in the reactive distillation column K1 is in the range from 0.2 bar to 5 bar, preferably from 0.5 bar to 4 bar, particularly preferably from 1 bar to 3 bar;

the temperature at the top of the reactive distillation column K1 is in the range from 25° C. to 125° C., preferably from 45° C. to 115° C., particularly preferably from 65° C. to 105° C.;

the temperature at the bottom of the reactive distillation column K1 is in the range from 110° C. to 255° C., preferably from 140° C. to 240° C., particularly preferably from 170° C. to 225° C.;

the diameter of the reactive distillation column K1 is determined by the throughput through the column. The calculation is carried out by the methods known to those skilled in the art. The throughput through the column correlates with the capacity of the OME plant;

the height of the column is in the range from 10 to 40 theoretical plates, preferably from 15 to 30 theoretical plates, particularly preferably from 20 to 25 theoretical plates. The conversion to the column height in meters is carried out for each of the separation-active internals described (trays, ordered packing, random packing elements) by the methods known to those skilled in the art;

below the feedpoint, the height of the reactive distillation column K1 is in the range from 3 to 20 theoretical plates, preferably from 4 to 15 theoretical plates, particularly preferably from 5 to 10 theoretical plates. The conversion to the height of the feedpoint in meters is carried out for each of the separation-active internals described (trays, ordered packing, random packing elements) by the methods known to those skilled in the art;

the reflux ratio in the reactive distillation column K1 is at least 0.20 g/g, for example at least 0.30 g/g or at least 0.40 g/g;

the ratio of volume of the liquid in the region between feedpoint and bottom offtake including possible side reactors and the bottom to the volume flow of the bottom offtake stream in the reactive distillation column K1 is at least 10 min; this ratio can also be more than 15 min or more than 30 min;

the reactive distillation column and its internals consist of conventional materials, with preference being given to steel;

the pH in the reactive distillation column K1 in the region between feedpoint and bottom offtake, including possible side reactors and the bottom, is in the range from 4 to 14, preferably from 5 to 14, particularly preferably from 7 to 14;

the pH in the reactive distillation column K1 in the region between feedpoint and overhead offtake plays no significant role;

the regulation of the pH in the reactive distillation column K1 in the region between feedpoint and bottom offtake is, if the pH is too low, effected by introduction of alkali, preferably by introduction of sodium methoxide in methanolic solution;

the feed to the columns can be either liquid or gaseous or both. Wet vapour is therefore likewise possible;

a downstream distillation column K2 having a conventional construction, which separates the OMEs having a chain length of n≥3 into the product $OME_{n=3-6}$ and a high-boiling fraction $OME_{n>6}$, is installed downstream of the reactive distillation column K1;

the high-boiling fraction from the column K2 is recirculated into the OME reactor;

the removal of water from the low boiler fraction occurs in conjunction with a downstream separation unit;

the separation unit for separating off the water is an apparatus known to those skilled in the art, preferably a pervaporation plant, vapour permeation plant or adsorption plant;

the low-water stream from the water separation is recirculated into the reactor;

the water-rich stream from the water separation, containing water together with formaldehyde, methanol, methylal and little $OME_{n=2-3}$, is optionally worked up further;

the optional work-up of the water-rich stream from the water separation is configured in such a way that methanol and methylal are obtained as overhead product from a distillation column K3 and are recirculated into the OME reactor and the bottom product containing water, formaldehyde and little $OME_{n=2-3}$ is preferably recirculated to a formaldehyde plant;

the aqueous solution of formaldehyde and methanol is fed as feedstream to the reactor, offgas streams from the various process steps can be recirculated to a formaldehyde plant, the process can be erected and operated on a "green field site" outside a conventional location, but is preferably operated in direct conjunction with a formaldehyde plant. Here, it is not necessary for the formaldehyde plant to make available the entire amount of formaldehyde required for the OME synthesis, but it should be able to accept the dilute recycle streams from the OME plant for utilization as material;

the process can be erected and operated in conjunction with other processes on one integrated site, preferably in conjunction with a methanol plant and formaldehyde plant and/or a refinery, preferably in conjunction with a formaldehyde plant, very particularly preferably in conjunction with a formaldehyde plant which operates by the silver contact process. As an alternative, the starting materials can be provided entirely or in part via a pipeline, ships or other logistic methods and the products can be shipped correspondingly;

the product produced can, for example, be used in the abovementioned applications, and in particular can be used either alone as diesel fuel or as part of diesel fuel, where the blending with other diesel fuels or mixtures thereof is carried out by static or dynamic mixing in devices known to those skilled in the art.

In a preferred embodiment, the column K1 has, in operation, the following features the pressure in the reactive distillation column K1 is from 0.2 bar to 5 bar;

the temperature at the top of the reactive distillation column K1 is from 25° C. to 125° C.;

the temperature at the bottom of the reactive distillation column K1 is from 110° C. to 255° C.;

the reactive distillation column K1 has from 10 to 40 theoretical plates, preferably from 15 to 30 theoretical plates, particularly preferably from 20 to 25 theoretical plates;

below the feedpoint, the reactive distillation column K1 has from 3 to 20 theoretical plates;

the reflux ratio in the reactive distillation column K1 is at least 0.20 g/g;

the ratio of volume of the liquid in the region between feedpoint and bottom offtake including any side reactors present and the bottom to the volume flow of the bottom offtake stream in the reactive distillation column K1 is at least 10 min;

the pH in the reactive distillation column K1 in the region between feedpoint and bottom offtake including any side reactors present and the bottom is in the range from 4 to 14.

In a particularly preferred embodiment, the column K1 has, in operation, the following features:

the pressure in the reactive distillation column K1 is from 0.5 to 4 bar;

the temperature at the top of the reactive distillation column K1 is from 45 to 115° C.;

the temperature at the bottom of the reactive distillation column K1 is from 140 to 240° C.;

the reactive distillation column K1 has from 5 to 30 theoretical plates;

below the feedpoint, the reactive distillation column K1 has from 4 to 15 theoretical plates;

the pH in the reactive distillation column K1 in the region between feedpoint and bottom offtake is in the range from 5 to 14.

In a very particularly preferred embodiment, the column K1 has, in operation, the following features:

the pressure in the reactive distillation column K1 is from 1 to 3 bar;

the temperature at the top of the reactive distillation column K1 is from 65 to 105° C.;

the temperature at the bottom of the reactive distillation column K1 is from 170 to 225° C.;

the reactive distillation column K1 has from 20 to 25 theoretical plates;

below the feedpoint, the reactive distillation column K1 has from 5 to 10 theoretical plates;

the pH in the reactive distillation column K1 in the region between feedpoint and bottom offtake is in the range from 7 to 14.

Catalysts in the solid phase in combination with liquid or gaseous starting materials have the advantage of ease of separation of the catalyst from the liquid or gaseous phase. Catalysts in the fluid phase often cannot be separated off completely from the fluid phase of the reaction mixture. For this reason, they remain partly in the reaction products and can lead to a reduction in the product quality. Furthermore, they can lead to precipitates, deposits and fouling in apparatuses. Fouling reduces the availability and thus the capacity of the plant. Due to the in-principle incomplete separation of the catalyst from the reaction mixture, the catalyst always has to be supplemented by additional further amounts. The recycling rate of a catalyst in the fluid phase within a process is always <100%. This adversely affects the economics of the overall process in the long term because of the losses of the expensive catalyst. This applies to processes which, for example, use liquid ionic liquids as catalyst or introduce a separate solvent in which a specific homogeneous catalyst is dissolved.

In general, in order to optimize the economics and to optimize and ensure high product quality, auxiliaries of any sort should be dispensed with as far as possible.

A person skilled in the art will know that the handling of liquid and gaseous materials in process apparatuses is preferred. They can be conveyed simply. The corresponding apparatuses can be obtained in a variety of forms in a large number. The apparatuses are not special constructions and can largely be scaled up without risk. Planning and erection of a large plant can accordingly be carried out inexpensively. The scaling up of the overall process is thus thoroughly possible. This brings economic advantages according to the rules of "economy of scale" with which a person skilled in the art will be familiar. Distillation columns are generally preferred as apparatuses in the design of industrial processes since distillation columns are the most frequent type of separation of materials in chemical technology. The design methods are generally widely tried and tested.

A person skilled in the art will know that in the distillation of formaldehyde-containing multicomponent mixtures containing water and methanol, reactions between water, methanol and formaldehyde lead to polyoxymethylene glycols and polyoxymethylene hemiformals (see reactions 2-5). The corresponding reactions are described in the literature (Hahnenstein I., Albert M., Hasse H., Kreiter C. G., Maurer G., NMR Spectroscopic and Densimetric Study of Reaction Kinetics of Formaldehyde Polymer Formation in Water, Deuterium Oxide, and Methanol, Industrial and Engineering Chemistry Research 1995, 34(2), 440-450). These mixtures have a complex phase behaviour. Numerous (reactive) azeotropes are formed, and these make separation of the reaction mixture difficult.

It has now surprisingly been found that OMEs having three and more oxymethylene units ($OME_{n\geq3}$) can be separated off quantitatively from the other components of the reactor output in a single distillative separation step. Here, quantitative means that at least 80%, preferably at least 85%, particularly preferably at least 90%, of the $OME_{n\geq3}$ is separated from the reactor output. This was initially not to be expected because of the similar boiling points of the $OME_{n\geq3}$ and the polyoxymethylene glycols (n≥3) and polyoxymethylene hemiformals (n≥3) inevitably present in the reactor output. Due to the complex interplay of reactions and distillation, polyoxymethylene glycols (n≥3) and polyoxymethylene hemiformals (n≥3) obviously react in the column to form the analogous species having a shorter chain length, which can then be separated off very well from the $OME_{n\geq3}$ by distillation.

The column K2 is generally a conventional distillation column for the physical separation of mixtures of materials, since the feedstream to the column K2 contains essentially no more formaldehyde, methanol and water.

The subsequent steps of water separation by, in particular, pervaporation, vapour permeation and/or adsorption are basic operations established in process engineering and are utilized, for example, for dewatering of the fuel components of bioethanol, as described in Frolkova A. K., Raeva V. M. Bioethanol dehydration: state of the art, Theoretical Foundations of Chemical Engineering, 2010 44 (4), 545-556.

US 2015/0053616 describes the possibility of dewatering of aqueous solutions containing formaldehyde and OME by means of pervaporation. The possibility of dewatering solutions containing formaldehyde, methanol and water by means of adsorption is likewise known, as described in Hasse H., Dampf-Flus sigkeitsgleichgewichte, Enthalpien und Reaktionskinetik in formaldehydhaltigen Mischungen, Ph. D Thesis, University of Kaiserslautem, Kaiserslautem 1990.

Adsorption and membrane processes can be scaled up on the industrial scale. Thus, adsorption plants having about 200 t of adsorbents have been industrially realized, as described in Baems M., Behr, A., Brehm A., Gmehling J., Hoffmann H., Onken U., Renken A., Technische Chemie, Wiley-VCH, Weinheim 2006.

Membrane processes are generally scaled up by increasing the installed membrane area, as described in Melin T., Rautenbach R., Membranverfahren, Grundlagen der Modul- und Anlagenauslegung, Springer-Verlag, Berlin, Heidelberg 2007.

The special feature of the process claimed is thus the combination of the abovementioned reactive distillation K1 with a reactor and the further skilful combination of reactor and reactive distillation with conventional steps for distillation and water separation, with all steps being scalable, and also the skilful utilization of recycle streams in the OME process itself or in external processes such as the preparation of formaldehyde.

A detailed sketch of a preferred embodiment of the process claimed is shown in FIG. 1.

Figure 1:
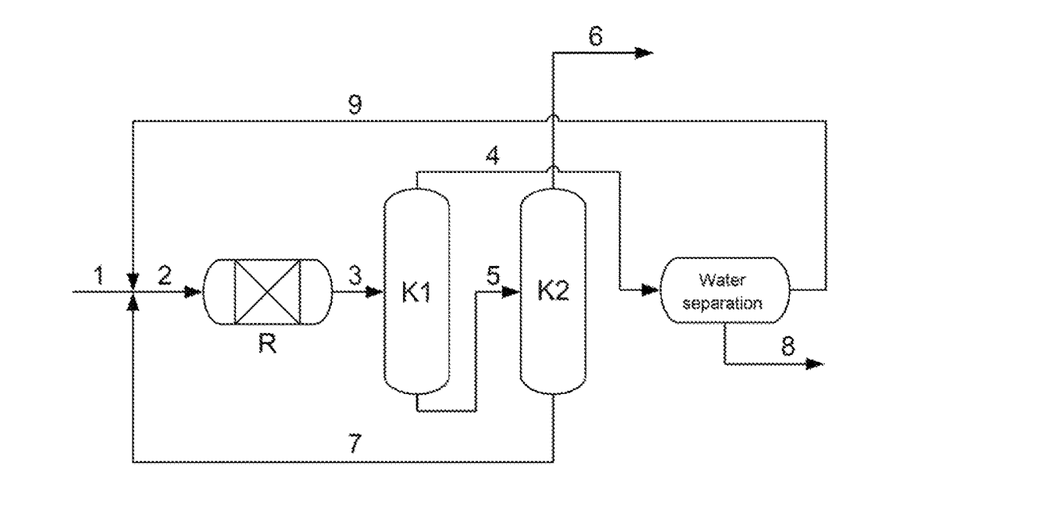
FIG. 1: Sketch of the process claimed. The FIGURE shows a preferred variant of the process of the invention.

In detail, the process comprises the steps:

(i) introduction of formaldehyde and of methanol, generally in the form of one or more aqueous solutions, (stream 1) and also the recycle streams 7 and 9 into a reactor and reaction to give a mixture (stream 3) containing formaldehyde, water, methylene glycol (MG), polyoxymethylene glycols ($MG_n$), methanol, hemiformals (HF), methylal ($OME_{n=1}$) and polyoxymethylene dimethyl ethers ($OME_{n>1}$); here, stream 2 is a mixture of streams 1, 7 and 9. The feedstream 1 can contain small amounts of further components (e.g. formic acid, methyl formate and further impurities known to those skilled in the art); in general, formaldehyde is introduced as aqueous formaldehyde solution having a formaldehyde content of from 20 to 95% by weight into the reactor R. Formaldehyde can also be introduced in highly concentrated, liquid or gaseous form or as paraformaldehyde in the form of a melt or as aqueous suspension into the OME synthesis reactor;

(ii) introduction of the reaction mixture (stream 3) into the specific reactive distillation column K1 and separation into a low boiler fraction containing essentially formaldehyde, water, methylene glycol (MG), polyoxymethylene glycols ($MG_n$), methanol, hemiformals (HF), methylal ($OME_{n=1}$) and polyoxymethylene dimethyl ethers ($OME_{n=2}$) (stream 4) and a high boiler fraction consisting essentially of polyoxymethylene dimethyl ethers ($OME_{n\geq3}$) (stream 5);

(iii) introduction of the high boiler fraction (stream 5) into the distillation column K2 and separation into a low boiler fraction (product fraction) containing the desired polyoxymethylene dimethyl ether $OME_{n=3-6}$ product (stream 6) and a high boiler fraction containing polyoxymethylene dimethyl ethers ($OME_{n>6}$) (stream 7);

(iv) recirculation of the high boiler fraction (stream 7) into the reactor;

(v) introduction of the low boiler fraction (stream 5) into an apparatus for water separation (preferably pervaporation, vapour permeation and adsorption) and separation into a low-water stream 9 and a water-rich stream 8;

(vi) recirculation of the low-water stream 9 into the reactor.

The water-rich stream 8 can be discharged from the process and optionally be recirculated into a formaldehyde plant.

The term "low-boiler fraction" is used for the mixture taken off in the upper part of the column, and the term "high boiler fraction" is used for the mixture taken off in the lower part. In general, the low boiler fraction is taken off at the top of the column, and the high boiler fraction is taken off at the bottom of the column. However, this is not absolutely necessary. Taking off the fractions via side offtakes in the stripping section and enrichment section of the column is likewise possible.

Here and in the following, "consisting essentially of" means that the fraction concerned comprises at least 90% by weight, preferably at least 95% by weight, of the components mentioned.

The reaction of formaldehyde with methanol to form OME occurs according to the net reaction equation (11).

$$nCH_2O + 2CH_3OH \leftrightarrow CH_3-O-(CH_2O)n\text{-}CH_3 + H_2O \quad \text{(Reaction 11)}$$

As solid catalysts, use is made of, for example, ion-exchange resins, zeolites, aluminosilicates, aluminium dioxide, titanium dioxide. Preference is given to ion-exchange resins, and particular preference is given to ion-exchange resins whose skeleton consists of sulfonated polystyrene (e.g. Amberlyst® 15, Amberlyst® 46). However, all solid catalysts which have an acidic centre generally come into question. The apparent residence time of the reaction mixture over the catalyst is in the range from 1 s to 7200 s, preferably from 5 s to 3600 s, particularly preferably from 8 s to 1800 s. The apparent residence time is defined here as the mass of the catalyst divided by the mass flow of the fluid which flows through the reactor. The reaction can be carried out in any apparatus which is suitable for carrying out reactions of fluid media over a fixed-bed catalyst: it can, for example, be carried out in the suspension mode in a continuous stirred tank reactor (CSTR), a tube reactor or a loop reactor. In a less preferred case, a reactive distillation can also be used. Preference is given to a fixed-bed reactor, e.g. a catalyst bed through which a single pass occurs, as for the OME synthesis from trioxane and methylal, described in Burger J., Ströfer E., Hasse H.: Production process for diesel fuel components poly(oxymethylene) dimethyl ethers from methane-based products by hierarchical optimization with varying model depth. Chemical Engineering Research and Design. 2013, 91(12), 2648-2662, a tray reactor or a shell-and-tube reactor or other apparatuses known to those skilled in the art. The temperature conditions in the reactor follow rules known to those skilled in the art. Owing to the comparatively small evolution of heat, the temperature can be regulated in a standard manner. The term "reactor" can encompass one or more apparatuses arranged in parallel or in series.

The product mixture can subsequently be brought into contact with an anion-exchange resin in order to obtain a substantially acid-free product mixture.

The reaction is generally carried out at a temperature of from 0 to 200° C., preferably from 30 to 150° C., particularly preferably from 40 to 120° C., and a pressure of from 0.3 to 30 bar, preferably from 1 to 20 bar, very particularly preferably from 1.2 to 10 bar. It is also possible to introduce the starting materials in gaseous form into a fixed-bed reactor. In this case, liquid starting materials have to be vaporized before entry into the reactor. As an alternative, gaseous feedstreams from an upstream production unit can be fed directly without intermediate condensation and after possible intermediate heating/cooling into the reactor. Such gaseous streams can, for example, be a gaseous reactor output stream containing formaldehyde and water from a formaldehyde plant. If the starting materials are fed in gaseous form into the fixed-bed reactor, condensation or partial condensation of the reactor output occurs before or in the work-up by distillation. This condensation or partial condensation can also occur even in the reactor itself when the temperature in the reactor goes below the dew point of oligomers formed due to the temperature conditions in the reactor.

The liquid reaction mixture forms polyoxymethylene glycols and polyoxymethylene hemiformals as coproducts even without addition of a catalyst. The condensation and chain-buildup reactions involved in the formation of the polyoxymethylene glycols, polyoxymethylene hemiformals and OMEs are equilibrium reactions and therefore also proceed (depending on the position of the chemical equilibrium) in the reverse direction as dissociation and chain-degradation reactions. The particular requirements which the reactive distillation column K1 has to meet are determined thereby.

Since the chemical reactions in the column K1 proceed at a finite reaction rate, the choice of suitable column internals is of great importance. Owing to the finite reaction rate of the chemical reactions, preference is given to using internals which make a high residence time and a high liquid content of the mixture in the column possible. If structured packings are used, specific banking-up packings as are described in EP 1 074 296 are particularly useful. If trays are used, specific residence time trays (e.g. Thormann® trays) are particularly useful. To increase the residence time, it is likewise conceivable to equip the column K1 with a side reactor or a plurality of side reactors. In this case, a side offtake stream is taken from the column for each side reactor and is introduced into a side vessel in which the chemical reactions can additionally proceed. The discharge stream from the side vessel is returned to the column.

The higher the concentration of formaldehyde in the feed to the column, the higher is the pressure in the column preferably selected in order to avoid precipitation of solids. Up to about 5% by weight of formaldehyde, the column is preferably operated at 1 bar. Above about 5% by weight of formaldehyde, the column is preferably operated as a pressure column.

Apart from the column K1, the further distillation columns are generally columns of conventional design. Columns containing random packing elements, tray columns and columns containing ordered packing and combinations thereof are possible, with preference being given to tray columns and columns containing ordered packing.

The distillation column K2 is operated at a pressure of from 0.01 to 1 bar, preferably at a pressure of from 0.05 to 0.9 bar and particularly preferably at a pressure of from 0.1 to 0.5 bar. The operating temperatures are generally in the range from 60 to 300° C. The column has from 5 to 40, preferably from 8 to 20, particularly preferably from 10 to 18, theoretical plates. The design of the column K2 is carried out in a standard manner according to rules known to those skilled in the art. The separation in the column K2 is described in the literature (Burger J., Ströfer E., Hasse H. Production process for diesel fuel components poly(oxymethylene) dimethyl ethers from methane-based products by hierarchical optimization with varying model depth. Chemical Engineering Research and Design. 2013, 91(12), 2648-2662).

Since the desired OMEs having a chain length of n=3-6 represent a middle-boiling fraction of the reactor output, it is likewise conceivable to integrate the two columns K1 and K2 in a single reactive dividing wall column in order to increase the efficiency of the overall process. Both the capital costs and the operating costs of the plant are decreased thereby. Such dividing wall columns are, for example, described in U.S. Pat. No. 5,914,012.

In this case, a dividing wall which extends continuously over the stripping section, the region of the feedstream and at least part of the enrichment section of the column is installed in the column. However, the dividing wall can also extend over, inter alia, the entire enrichment section. In this reactive dividing wall column, a mixture of formaldehyde, methanol, water, methylal and $OME_{n=2}$ is obtained as overhead product. The side product which is taken off from the column at the height of the feedpoint or between the feedpoint and the bottom on the side of the dividing wall opposite the feedpoint is the desired product stream containing OMEs having a chain length of n=3-6. The OMEs having chain lengths of n≥6 are obtained at the bottom of the column. This reactive dividing wall column is operated at a pressure of from 0.01 to 5 bar, preferably at a pressure of from 0.05 to 4 bar and particularly preferably at a pressure of from 0.01 to 3 bar. The operating temperatures are essentially analogous to the temperatures when the columns K1 and K2 are operated individually. The column has from 15 to 80, preferably from 30 to 50, particularly preferably from 35 to 40, theoretical plates. Here, from 10 to 30, preferably from 15 to 25, theoretical plates are in the region having the installed dividing wall.

To increase the energy efficiency of the process, it is possible to couple the distillation columns thermally. Here, for example, the vapour from one column is used for heating another column as a result of suitable temperature and pressure conditions in the columns. It is likewise conceivable to compress the vapours from the columns and utilize them as heating medium for various vaporizers in the process. It is likewise conceivable to couple the plant in terms of energy with other plants in the integrated facility, preferably with a formaldehyde plant. The heat of reaction removed from the formaldehyde reactor can, for example, be used for generating heating steam for the OME plant.

Stream 6 represents the product of value from the process of the invention. It contains more than 95% by weight of $OME_{n=3-6}$, preferably more than 98% by weight of $OME_{n=3-6}$, very particularly preferably more than 99% of $OME_{n=3-6}$.

In the case of the water separation being configured as a pervaporation or vapour permeation plant, it is possible to use inorganic and polymeric membranes. Possible polymeric membranes are, for example: polyamide, polyamidimide, polyacrylonitrile, polybenzimidazole, polyester, polycarbonate, polyetherimide, polyethylenimine, polyimide, polymethyl methacrylate, polypropylene, polysulfone, polyether sulfone, polyphenyl sulfone, polytetrafluoroethylene, poly-vinylidene fluoride, polyvinylpyrrolidone, polyvinyl alcohol, polydimethylsiloxane. The degree of crosslinking of the polymeric membrane can be set freely. The mechanical stability of the membranes can be increased by a support layer. Possible inorganic membranes are, for example: zeolites, metal oxides such as aluminium dioxide, zirconium dioxide, silicon dioxide, titanium oxide and glass. The pore structure of the membranes can be either symmetric or asymmetric. Preference is given to using inorganic membranes, with particular preference being given to using inorganic zeolites as membrane. The arrangement of the membrane modules is preferably, but not necessarily, a "Christmas tree structure". As a result, all membrane modules used are equally loaded hydrodynamically. Possible membrane modules are all module forms known to those skilled in the art, for example tube modules, plate modules, capillary modules and hollow fibre modules. If polymeric membranes are used, plate modules are preferred. If inorganic membranes are used, tube modules are preferred.

The operating pressure on the feed side of the membrane is in the range from 0.1 to 200 bar, preferably from 1 to 150 bar. The pressure on the permeate side is in the range from 0.001 to 10 bar, preferably from 0.01 to 5 bar. The temperature is in the range from 30 to 200° C. A person skilled in the art will know that, particularly in the case of pervaporation, heating of the retentate streams by means of intermediate heat exchangers is generally carried out between the membrane modules. In particular, it is possible to use the retentate stream from the last membrane module for preheating the feed to the first membrane module.

Depending on the pressure selected on the permeate side of the membrane, condensation of the permeate stream is effected by means of cooling water or cooling brine. Other process streams from the OME plant or a formaldehyde plant can likewise be used. Cooling brine is preferably used in the case of very low pressures on the permeate side. If a vacuum is applied on the permeate side, it is possible to use either a mechanical vacuum pump or a thermally operating vacuum pump. In the latter case, a jet compressor is preferably used.

If a vapour permeation plant is used, it is possible to operate the column K1 with only a partial condenser, so that the uncondensed vapour from the column K1 is conveyed directly into the vapour permeation plant. However, it is furthermore also possible to operate the column K1 with a total condenser and vaporize the feedstream to the vapour permeation plant beforehand by means of an additional heat exchanger.

In the case of the water separation being configured as an adsorption plant, all conventional adsorbents can be used. Examples are zeolites, activated carbon, adsorber resins, metal oxides such as aluminium oxide, zirconium dioxide, silicon dioxide (silica gels) and titanium oxide, salts such as magnesium sulfate, sodium sulfate, calcium hydride, calcium oxide, calcium sulfate, potassium carbonate, potassium hydroxide, copper sulfate, lithium aluminium hydride, sodium hydroxide, and elemental alkali metals and alkaline earth metals. Preference is given to using zeolites and metal oxides, with very particular preference being given to using zeolites. The preferred adsorbents can be regenerated particularly simply by means of suitable temperature and pressure conditions. If zeolites are used as adsorbents, preference is given to using zeolites of the type NaA, particularly preferably zeolites of the type NaA whose pore width is in the range from 2 to 10 Angström. In discontinuous operation, the water-rich stream F6 is obtained in the regeneration of the adsorber. Thus, water and the additionally adsorbed components desorb.

The adsorption plant is preferably configured as a simple fixed-bed plant. However, all further types of adsorbers known to those skilled in the art are possible. In this case, regeneration of the adsorbent is preferably effected by means of a pressure and/or temperature change in discontinuous operation. For this reason, two adsorber fixed beds are generally required, so that during operation of one fixed bed, the other fixed bed can be regenerated. An arrangement having ≥3 adsorber beds operated in parallel is usual. The feedstream to the adsorber can be either gaseous or liquid.

It is also conceivable to recirculate the stream 4 directly, without water separation, to a formaldehyde plant and carry out the water separation in the formaldehyde plant. Here, not only methanol but also full acetals from stream 4 react in the formaldehyde synthesis reactor to form formaldehyde and water (Masamoto J., Matsuzaki K., Development of methylal synthesis by reactive distillation; Journal of Chemical Engineering of Japan, 1994, 27(1), 1-5). The water separation can be effected by subsequent concentration of the formaldehyde solution obtained, as is described, for example, in U.S. Pat. Nos. 7,342,139; 7,345,207; 7,273,955; 7,193,115; 6,610,888; 7,414,159. The solution which has been concentrated is again provided for the OME synthesis in the reactor of the OME synthesis. It is also possible, as described in U.S. Pat. No. 7,390,932, to prepare highly concentrated formaldehyde in the gas phase and feed this to the reactor. Furthermore, the aqueous formaldehyde solution can be converted by known methods into paraformaldehyde, which is introduced as melt or suspension of solid into the reactor. Regardless of the recirculation of the stream 4, highly concentrated liquid or gaseous formaldehyde or paraformaldehyde as melt or suspension can also be used in the OME synthesis reactor.

Apart from the preferred starting material methanol, derivatives of methanol, e.g. methylal, dimethyl ether, $OME_2$ and/or mixtures of these with one another and/or with methanol, can also be used as reaction partners for formaldehyde in the OME synthesis.

Apart from methanol as simplest alcohol and derivatives thereof, it is in principle also possible to use other alcohols, e.g. ethanol, propanol and butanol and/or mixtures of these and/or with methanol, as reaction partners for the formaldehyde. What has been said above about the derivatives of methanol applies analogously to the derivatives of other alcohols, with mixed derivatives such as $C_2H_5O-CH_2-OCH_3$ or $C_2H_5-O-CH_3$ also being possible. In the case of miscibility gaps, emulsions are used.

The process of the invention can be operated entirely or partly continuously or batchwise. This also applies to the reactor and the columns. Preference is given to continuous operation of the process. Units such as the water separation by adsorption, which are generally preferably operated batchwise in the industry, are configured in a plurality of apparatuses connected in parallel so that a virtually continuous flow of all streams through this unit is possible.

The invention further provides the products obtainable by the process of the invention and also the blends of these products with fuel and oil fractions from a refinery or an integrated refinery site. These blends can additionally contain fuel auxiliaries and additives as are known to a person skilled in the field of fuel.

The composition of a mixture of OME oligomers is, when the reactor of the process is operated close to the point of equilibrium conversion: $0.35$ g/g$\leq x_{OME3}\leq 0.79$ g/g, $0.17$ g/g$\leq x_{OME4}\leq 0.36$ g/g, $0.04$ g/g$\leq x_{OME5}\leq 0.31$ g/g, $x_{OME6}\leq 0.06$ g/g, preferably $0.37$ g/g$\leq x_{OME3}\leq 0.70$ g/g; $0.23$ g/g$\leq x_{OME4}\leq 0.35$ g/g, $0.07$ g/g$\leq x_{OME5}\leq 0.26$ g/g, $x_{OME6}\leq 0.08$ g/g, very particularly preferably $0.40$ g/g$\leq x_{OME3}\leq 0.62$ g/g, $0.26$ g/g, $\leq x_{OME4}\leq 0.35$ g/g, $0.11$ g/g$\leq x_{OME5}\leq 0.26$ g/g, $x_{OME6}\leq 0.12$ g/g. Here, $x_{OMEn}$ is the mass fraction of OME oligomers having n oxymethylene units, based on the mass of the mixture.

Here, "close to equilibrium" means that no concentration of the abovementioned individual OME species is more than 40% away from the value corresponding to the composition of a reaction mixture which is in thermodynamic equilibrium.

The composition of this mixture of OME oligomers is a consequence of the above-described process conditions.

However, depending on customer demand, other mixtures of OME oligomers can also be prepared. This preparation is carried out by varying the process conditions in the reactor and in particular the position of the separation cuts in the columns. The recycle streams then have to be adapted appropriately and the process no longer operates at the economic and ecological optimum.

A further separation of the $OME_{n=3-6}$ product according to chain length can be effected by process engineering operations, for example distillation. The design of a distillation sequence for the separation of $OME_{n=3-6}$ according to chain length can in this case be carried out in a standard manner. Preference is given to $OME_3$ being obtained as overhead product from a first distillation column, $OME_4$ being obtained as overhead product from a second distillation column, $OME_5$ being obtained as overhead product from a third distillation column and $OME_6$ being obtained as bottom product from the third distillation column (but this is not absolutely necessary). However, the optional separation of the $OME_{n=3-6}$ product does not change the above-described distribution of the OME oligomers relative to one another, since the ratios of the OME chain lengths are influenced only insignificantly by the separation due to the separation steps which are in reality not perfectly sharp.

The invention is illustrated by the following examples.

EXAMPLES

Example 1

Overall Process

Table 1 to Table 4 show four typical stream series of a preferred variant of the claimed process within measurement accuracy. The numbers have been appropriately rounded. Here, the mass fraction 0.00 g/g means a mass fraction of <0.005 g/g. In Table 1 to Table 3, the mass ratio of formaldehyde to methanol in stream 1 is 1.65. The proportion of water in stream 1 was varied between 0.05 g/g (Table 1), 0.10 g/g (Table 2) and 0.20 g/g (Table 3). In Table 4, the mass ratio of formaldehyde to methanol in stream 1 is 1.60. The proportion of water in stream 1 is 0.10 g/g.

The water separation was in all cases dimensioned so that the proportion of water in stream 9 is about 0.02 g/g. Since the proportion of water in stream 1 was increased from Table 1 to Table 3 so that the proportion by mass of water in stream 9 is constant, the installed membrane area in the case of the water separation being configured as vapour permeation or pervaporation plant was generally increased and in the case of the water separation being configured as adsorption plant, the mass of adsorbent was increased.

However, since the experiments were carried out on the micro scale, the increase in the membrane area is negligibly small in this example.

The mass flow and the composition of stream 8 (discharged water stream) can vary as a function of the configuration of the water separation. In the tables, stream 8 (not shown) is given by the difference between streams 4 and 9.

TABLE 1

Example (case 1) for a stream series of the process of the invention; feed composition (stream 1):proportion of water = 0.05 g/g, mass ratio of formaldehyde to methanol = 1.65

| | Stream | | | | | | | |
|---|---|---|---|---|---|---|---|---|
| | 1 | 2 | 3 | 4 | 5 | 6 | 7 | 9 |
| Mass flow/(kg/h) | 1.2 | 6.1 | 6.1 | 5.0 | 1.1 | 1.0 | 0.1 | 4.8 |
| | Mass fractions/(g/g) | | | | | | | |
| Formaldehyde | 0.59 | 0.36 | 0.25 | 0.30 | 0.00 | 0.00 | 0.00 | 0.32 |
| Methanol | 0.36 | 0.20 | 0.13 | 0.16 | 0.00 | 0.00 | 0.00 | 0.17 |
| Water | 0.05 | 0.03 | 0.04 | 0.05 | 0.00 | 0.00 | 0.00 | 0.02 |
| Methylal | 0.00 | 0.24 | 0.24 | 0.29 | 0.00 | 0.00 | 0.00 | 0.30 |
| $OME_2$ | 0.00 | 0.15 | 0.15 | 0.19 | 0.00 | <0.02 | 0.00 | 0.19 |
| $OME_3$ | 0.00 | 0.00 | 0.09 | <0.01 | 0.47 | 0.54 | 0.00 | 0.00 |
| $OME_4$ | 0.00 | 0.00 | 0.05 | 0.00 | 0.26 | 0.30 | 0.00 | 0.00 |
| $OME_5$ | 0.00 | 0.00 | 0.03 | 0.00 | 0.14 | 0.16 | 0.00 | 0.00 |
| $OME_6$ | 0.00 | 0.01 | 0.01 | 0.00 | 0.07 | <0.02 | 0.56 | 0.00 |
| $OME_7$ | 0.00 | 0.01 | 0.01 | 0.00 | 0.04 | 0.00 | 0.29 | 0.00 |
| $OME_8$ | 0.00 | 0.00 | 0.00 | 0.00 | 0.02 | 0.00 | 0.15 | 0.00 |

For the stream series of Table 1 (case 1), an experimental plant was operated on the micro scale. A fixed-bed reactor containing 200 g of the heterogeneous catalyst Amberlyst® 46 which had previously been flushed with methanol was used as reactor. The reactor was operated at 60° C. The reactive distillation column K1 was equipped with the structured packing Sulzer CY having 20 theoretical plates. The feed was introduced at the level of plate 10. The pressure in the column K1 was 2 bar. The temperature at the top of the column K1 was 85° C., and the temperature at the bottom was 200° C. The column K1 was operated with a reflux ratio of 1.0 kg/kg. The temperature of the feed to the column K1 corresponded to the reactor temperature of 60° C. The column K2 was equipped with the structured laboratory packing Sulzer DX having 15 theoretical plates. The feed was introduced at plate 8 with a temperature of likewise 60° C. The pressure in the column K2 was 0.1 bar. The temperature at the top of the column K2 was 97° C., and the temperature at the bottom was 203° C. The column K2 was operated with a reflux ratio of 0.8 kg/kg. The water separation was carried out by means of pervaporation. As membrane, a membrane composed of NaA zeolite having a pore width of 4.2 Å was used. The effective membrane area was about 2 m$^2$. The pervaporation was carried out at 70° C. and a feed pressure of 2 bar. A vacuum of 50 mbar was established on the permeate side. The experimental plant was operated for 8 hours in continuous operation.

TABLE 2

Example (case 2) of a stream series of the process claimed; feed composition (stream 1):proportion of water = 0.10 g/g; mass ratio of formaldehyde to methanol = 1.65

| | Stream | | | | | | | |
|---|---|---|---|---|---|---|---|---|
| | 1 | 2 | 3 | 4 | 5 | 6 | 7 | 9 |
| Mass flow/(kg/h) | 1.2 | 6.5 | 6.5 | 5.4 | 1.1 | 1.0 | 0.1 | 5.1 |
| | Mass fractions/(g/g) | | | | | | | |
| Formaldehyde | 0.56 | 0.37 | 0.27 | 0.32 | 0.00 | 0.00 | 0.00 | 0.34 |
| Methanol | 0.34 | 0.20 | 0.14 | 0.17 | 0.00 | 0.00 | 0.00 | 0.18 |
| Water | 0.10 | 0.03 | 0.05 | 0.06 | 0.00 | 0.00 | 0.00 | 0.02 |
| Methylal | 0.00 | 0.22 | 0.22 | 0.27 | 0.00 | 0.00 | 0.00 | 0.29 |
| OME$_2$ | 0.00 | 0.14 | 0.14 | 0.17 | 0.00 | <0.02 | 0.00 | 0.18 |
| OME$_3$ | 0.00 | 0.00 | 0.08 | <0.01 | 0.47 | 0.54 | 0.00 | 0.00 |
| OME$_4$ | 0.00 | 0.00 | 0.05 | 0.00 | 0.26 | 0.30 | 0.00 | 0.00 |
| OME$_5$ | 0.00 | 0.00 | 0.02 | 0.00 | 0.14 | 0.16 | 0.00 | 0.00 |
| OME$_6$ | 0.00 | 0.01 | 0.01 | 0.00 | 0.07 | <0.02 | 0.56 | 0.00 |
| OME$_7$ | 0.00 | 0.01 | 0.01 | 0.00 | 0.04 | 0.00 | 0.29 | 0.00 |
| OME$_8$ | 0.00 | 0.00 | 0.00 | 0.00 | 0.02 | 0.00 | 0.15 | 0.00 |

For the stream series of Table 2 (case 2), an experimental plant was operated on the micro scale. The temperature at the top of the reactive distillation column K1 was in this case 89° C., and the temperature at the bottom was 202° C. The operating parameters of all other apparatuses correspond to those of case 1 within the limits of measurement accuracy. In particular, the temperatures at the top and bottom of the column K2 are the same because of the similar composition of the feedstream 5.

TABLE 3

Example (case 3) of a stream series of the process claimed; Feed composition (stream 1):proportion of water = 0.20 g/g; mass ratio of formaldehyde to methanol = 1.65

| | Stream | | | | | | | |
|---|---|---|---|---|---|---|---|---|
| | 1 | 2 | 3 | 4 | 5 | 6 | 7 | 9 |
| Mass flow/(kg/h) | 1.4 | 7.3 | 7.3 | 6.2 | 1.1 | 1.0 | 0.1 | 5.8 |
| | Mass fractions/(g/g) | | | | | | | |
| Formaldehyde | 0.50 | 0.39 | 0.30 | 0.35 | 0.00 | 0.00 | 0.00 | 0.38 |
| Methanol | 0.30 | 0.21 | 0.15 | 0.18 | 0.00 | 0.00 | 0.00 | 0.19 |
| Water | 0.20 | 0.05 | 0.07 | 0.08 | 0.00 | 0.00 | 0.00 | 0.02 |
| Methylal | 0.00 | 0.20 | 0.20 | 0.24 | 0.00 | 0.00 | 0.00 | 0.25 |
| OME$_2$ | 0.00 | 0.13 | 0.13 | 0.15 | 0.00 | <0.02 | 0.00 | 0.16 |
| OME$_3$ | 0.00 | 0.00 | 0.07 | <0.01 | 0.47 | 0.54 | 0.00 | 0.00 |
| OME$_4$ | 0.00 | 0.00 | 0.04 | 0.00 | 0.26 | 0.30 | 0.00 | 0.00 |
| OME$_5$ | 0.00 | 0.00 | 0.02 | 0.00 | 0.14 | 0.16 | 0.00 | 0.00 |
| OME$_6$ | 0.00 | 0.01 | 0.01 | 0.00 | 0.07 | <0.02 | 0.56 | 0.00 |
| OME$_7$ | 0.00 | 0.01 | 0.01 | 0.00 | 0.04 | 0.00 | 0.29 | 0.00 |
| OME$_8$ | 0.00 | 0.00 | 0.00 | 0.00 | 0.02 | 0.00 | 0.15 | 0.00 |

For the stream series of Table 3 (case 3), an experimental plant was operated on the micro scale. The temperature at the top of the reactive distillation column K1 was in this case 91° C., the temperature at the bottom was 202° C. The operating parameters of all other apparatuses correspond to those of case 1 within the limits of measurement accuracy. In particular, the temperatures at the top and bottom of the column K2 are the same because of the similar composition of the feedstream 5.

TABLE 4

Example (case 4) of a stream series of the process claimed; feed composition (stream 1):proportion of water = 0.1 g/g; mass ratio of formaldehyde to methanol = 1.60.

| | Stream | | | | | | | |
|---|---|---|---|---|---|---|---|---|
| | 1 | 2 | 3 | 4 | 5 | 6 | 7 | 9 |
| Mass flow/(kg/h) | 1.2 | 8.0 | 8.0 | 6.9 | 1.1 | 1.0 | 0.1 | 6.7 |
| | Mass fractions/(g/g) | | | | | | | |
| Formaldehyde | 0.55 | 0.27 | 0.19 | 0.22 | 0.00 | 0.00 | 0.00 | 0.22 |
| Methanol | 0.35 | 0.18 | 0.13 | 0.15 | 0.00 | 0.00 | 0.00 | 0.16 |
| Water | 0.10 | 0.03 | 0.05 | 0.05 | 0.00 | 0.00 | 0.00 | 0.02 |
| Methylal | 0.00 | 0.33 | 0.33 | 0.39 | 0.00 | 0.00 | 0.00 | 0.40 |
| OME$_2$ | 0.00 | 0.17 | 0.17 | 0.19 | 0.00 | <0.02 | 0.00 | 0.20 |
| OME$_3$ | 0.00 | 0.00 | 0.08 | <0.01 | 0.57 | 0.62 | 0.00 | 0.00 |
| OME$_4$ | 0.00 | 0.00 | 0.03 | 0.00 | 0.25 | 0.27 | 0.00 | 0.00 |
| OME$_5$ | 0.00 | 0.00 | 0.01 | 0.00 | 0.11 | 0.11 | 0.00 | 0.00 |
| OME$_6$ | 0.00 | 0.01 | 0.01 | 0.00 | 0.04 | <0.02 | 0.64 | 0.00 |
| OME$_7$ | 0.00 | 0.00 | 0.00 | 0.00 | 0.02 | 0.00 | 0.26 | 0.00 |
| OME$_8$ | 0.00 | 0.00 | 0.00 | 0.00 | 0.01 | 0.00 | 0.10 | 0.00 |

For the stream series of Table 4 (case 4), an experimental plant was operated on the micro scale. The temperature at the top of the column K1 was in this case 82° C., the temperature at the bottom was 195° C. The temperature at the top of the column K2 was in this case 94° C., and the temperature at the bottom was 200° C. The operating parameters of all other apparatuses correspond to those of case 1 within the limits of measurement accuracy.

Example 2

Operation of the Special Reactive Distillation Column K1

The operating parameters of an embodiment of the special reactive distillation column K1 are summarized in Table 5. Here, the mass fraction 0.00 g/g means a mass fraction of <0.005 g/g. The column was here supplied with a feed having the composition of stream 3 in Table 2 at plate 12. For this feed, the minimum number of theoretical plates required is in the range from 10 to 18, depending on the desired yield of $OME_{n \geq 3}$ at the bottom of the column. The column was operated at 2 bar and a reflux ratio of 1.0 kg/kg, and the number of theoretical plates is 30 (including vaporizer and condenser). The structured packing Sulzer CY having a specific surface area of 700 $m^2/m^3$ was used as separation-active internal. The diameter of the column was 53 mm and the liquid content at each theoretical plate was in the range from 10 to 80 ml of liquid. This corresponds to from 1% to 8% of the empty tube volume. In addition, special collection trays and liquid distributors were installed between each section in order to make a long residence time of the mixture in the column possible.

TABLE 5

Operating parameters for an embodiment of the special reactive distillation column K1 at p = 2 bar.

|  | Feed | Bottom product | Overhead product |
|---|---|---|---|
| Temperature/(° C.) | 60 | 202 | 89 |
| Mass flow/(kg/h) | 1.10 | 0.19 | 0.91 |
| Mass fractions/(g/g) | | | |
| Formaldehyde | 0.27 | <0.01 | 0.33 |
| Methanol | 0.14 | <0.01 | 0.17 |
| Water | 0.05 | <0.01 | 0.06 |
| Methylal | 0.22 | <0.01 | 0.27 |
| $OME_2$ | 0.14 | 0.00 | 0.17 |
| $OME_3$ | 0.08 | 0.43 | <0.01 |
| $OME_4$ | 0.05 | 0.28 | 0 |
| $OME_5$ | 0.02 | 0.11 | 0 |
| $OME_6$ | 0.01 | 0.06 | 0 |
| $OME_7$ | 0.01 | 0.06 | 0 |
| $OME_8$ | 0.01 | 0.06 | 0 |

In the same column, an additional distillation experiment was carried out with a feed having the composition of stream 3 of Table 4 being fed in at plate 12. This represents a further embodiment of the special reactive distillation column K1. For this feed, the minimum number of theoretical plates required is in the range from 5 to 13, depending on the desired yield of $OME_{n \geq 3}$ at the bottom of the column. The column was operated at 1.6 bar and a reflux ratio of 0.9 kg/kg, and the number of theoretical plates was once again 30 (including vaporizer and condenser). The liquid content at each theoretical plate was in the range from 10 to 80 ml of liquid. This corresponds to from 1% to 8% of the empty tube volume. The operating parameters of this column are summarized in Table 6.

In both embodiments of the specific reactive distillation column, $OME_{n \geq 3}$ can be obtained in a very high yield at the bottom of the column.

TABLE 6

Operating parameters for an embodiment of special reactive distillation column K1 at p = 1.6 bar

|  | Feed | Bottom product | Overhead product |
|---|---|---|---|
| Temperature/(° C.) | 60 | 185 | 75 |
| Mass flow/(kg/h) | 1.20 | 0.16 | 1.04 |
| Mass fractions/(g/g) | | | |
| Formaldehyde | 0.19 | <0.01 | 0.22 |
| Methanol | 0.13 | <0.01 | 0.15 |
| Water | 0.05 | <0.01 | 0.05 |
| Methylal | 0.33 | <0.01 | 0.38 |
| $OME_2$ | 0.17 | 0.00 | 0.19 |
| $OME_3$ | 0.08 | 0.56 | <0.01 |
| $OME_4$ | 0.03 | 0.26 | 0 |
| $OME_5$ | 0.01 | 0.11 | 0 |
| $OME_6$ | 0.01 | 0.05 | 0 |
| $OME_7$ | 0.00 | 0.02 | 0 |
| $OME_8$ | 0.00 | 0.01 | 0 |

Example 3

Water Separation by Means of Adsorption

In a batch shaken flask experiment, four different liquid mixtures consisting of formaldehyde, water, methanol, methylal, $OME_2$ and $OME_3$ were brought into contact with the adsorbent zeolite 3A at a temperature of 25° C. Here, the proportion by weight of water was systematically varied, while the ratios of all other components remained constant. The mass ratio of liquid to adsorbent is 2:1. The composition was measured before and after the adsorption procedure. The results are shown in Table 7 (before adsorption) and Table 8 (after adsorption). It can be seen here that the proportion by mass of water has been significantly reduced by addition of the adsorbent. The adsorbent was subsequently regenerated at a temperature of >50° C. and a pressure of <500 mbar and could be reused.

TABLE 7

Compositions of the liquid mixtures before adsorption.

|  | Mixture | | | |
|---|---|---|---|---|
|  | 1 | 2 | 3 | 4 |
| Mass fractions/(g/g) | | | | |
| Formaldehyde | 0.21 | 0.19 | 0.18 | 0.17 |
| Methanol | 0.29 | 0.27 | 0.25 | 0.24 |
| Water | 0.01 | 0.07 | 0.12 | 0.16 |
| Methylal | 0.30 | 0.28 | 0.26 | 0.25 |
| $OME_2$ | 0.20 | 0.19 | 0.18 | 0.17 |

TABLE 8

Compositions of the liquid mixtures after adsorption

|  | Mixture | | | |
|---|---|---|---|---|
|  | 1 | 2 | 3 | 4 |
| Mass fractions/(g/g) | | | | |
| Formaldehyde | 0.21 | 0.20 | 0.19 | 0.19 |
| Methanol | 0.27 | 0.28 | 0.27 | 0.26 |
| Water | 0.00 | 0.02 | 0.05 | 0.09 |
| Methylal | 0.30 | 0.28 | 0.29 | 0.27 |
| $OME_2$ | 0.21 | 0.21 | 0.20 | 0.19 |

Example 4

Water Separation by Means of a Membrane Process

In a laboratory pervaporation plant, a membrane composed of NaA zeolite having a pore width of 4.2 Å was supplied with a feedstream corresponding to the composition of stream 4 of Table 4. The feed pressure was 2 bar, and a vacuum of 50 mbar was set on the permeate side. The pervaporation was carried out at 80° C. and the effective membrane area is 70 cm$^2$. The permeate stream was cooled by means of a cold trap using liquid nitrogen and subsequently analysed. The proportion by mass of water in the permeate stream was >0.95 g/g. Methanol, formaldehyde and methylal were also detected in addition to water in the permeate stream.

The invention claimed is:

1. Process for preparing polyoxymethylene dimethyl ethers having ≥3 oxymethylene units ($OME_{n\geq3}$), comprising the steps:
   (i) introduction of formaldehyde, methanol and water into a reactor R and reaction to give a reaction mixture containing formaldehyde, water, methylene glycol, polyoxymethylene glycols, methanol, hemiformals, methylal ($OME_{n=1}$) and polyoxymethylene dimethyl ethers ($OME_{n>1}$); and
   (ii) introduction of the reaction mixture into a reactive distillation column K1 having a feedpoint, a bottom offtake, and an overhead offtake and separation into a low boiler fraction F1 containing formaldehyde, water, methylene glycol, polyoxymethylene glycols, methanol, hemiformals, methylal ($OME_{n=1}$) and polyoxymethylene dimethyl ethers having from 2 to 3 oxymethylene units ($OME_{n=2-3}$) and a high boiler fraction F2 containing essentially polyoxymethylene dimethyl ethers having more than two oxymethylene units ($OME_{n\geq3}$), wherein the high boiler fraction F2 contains at least 90% by weight of polyoxymethylene di-methyl ethers having more than 2 oxymethylene units ($OME_{n\geq3}$), wherein the ratio of a volume of the liquid in the region between feedpoint and bottom offtake including any side reactors present and the bottom to the volume flow of the bottom offtake stream in the reactive distillation column K1 is at least 10 min, wherein the low boiler fraction F1 and the high boiler fraction F2 are withdrawn from the reactive distillation column K1.

2. Process according to claim 1 for preparing polyoxymethylene dimethyl ethers having 3 to 6 oxymethylene units ($OME_{n=3-6}$), comprising the steps:
   (i) introduction of formaldehyde, methanol and water into a reactor R and reaction to give a reaction mixture containing formaldehyde, water, methylene glycol, polyoxymethylene glycols, methanol, hemiformals, methylal ($OME_{n=1}$) and polyoxymethylene dimethyl ethers ($OME_{n>1}$);
   (ii) introduction of the reaction mixture into a reactive distillation column K1 and separation into a low boiler fraction F1 containing formaldehyde, water, methylene glycol, polyoxymethylene glycols, methanol, hemiformals, methylal ($OME_{n=1}$) and polyoxymethylene dimethyl ethers having from 2 to 3 oxymethylene units ($OME_{n=2-3}$) and a high boiler fraction F2 containing essentially polyoxymethylene dimethyl ethers having more than two oxymethylene units ($OME_{n\geq3}$);
   (iii) introduction of the high boiler fraction F2 into a distillation column K2 and separation into a product fraction F3 containing polyoxymethylene dimethyl ethers having from 3 to 6 oxymethylene units ($OME_{n=3-6}$) and a high boiler fraction F4 containing polyoxymethylene dimethyl ethers having more than 6 oxymethylene units ($OME_{n>6}$);
   (iv) optionally recirculation of the high boiler fraction F4 into the reactor R.

3. Process according to claim 1, characterized in that the high boiler fraction F2 contains at least 95% by weight of polyoxymethylene dimethyl ethers having more than two oxymethylene units ($OME_{n\geq3}$).

4. Process according to claim 2, characterized in that the product fraction F3 contains more than 95% by weight of polyoxymethylene dimethyl ethers having from 3 to 6 oxymethylene units ($OME_{n=3-6}$).

5. Process according to claim 1 comprising the additional steps:
   (v) introduction of the low boiler fraction F1 into an apparatus for water separation and removal of water or a water-rich stream F6, giving a low-water stream F5;
   (vi) optionally recirculation of the low-water stream F5 into the reactor.

6. Process according to claim 5 comprising the additional step:
   (vii) distillation of the water-rich stream F6 to give a stream F7 which contains methanol and methylal and is recirculated into the reactor R and a stream F8 containing water, formaldehyde and polyoxymethylene dimethyl ethers having from 2 to 3 oxymethylene units ($OME_{n=2-3}$).

7. Process according to claim 2, characterized in that the columns K1 and K2 are configured as a single reactive distillation dividing wall column, with the low boiler fraction F1 being obtained as overhead offtake stream, the product fraction F3 being obtained as side offtake stream and the high boiler fraction F4 being obtained as bottom offtake stream from the dividing wall column.

8. Process according to claim 1, characterized in that formaldehyde is introduced as aqueous formaldehyde solution having a formaldehyde content of from 20 to 95% by weight into the reactor R.

9. Process according to claim 1, characterized in that formaldehyde is introduced as paraformaldehyde as melt or suspension into the reactor R.

10. Process according to claim 1, characterized in that the reaction in step (i) is carried out in the presence of a solid catalyst selected from the group consisting of ion-exchange resins, zeolites, aluminosilicates, aluminium dioxide and titanium dioxide.

11. Process according to claim 1, characterized in that the pH in the reactive distillation column K1 is from 4 to 14.

12. Process according to claim 5, characterized in that the apparatus used for water separation in step (v) is a pervaporation, vapour permeation or adsorption plant.

13. Process according to claim 1, characterized in that the reactive distillation column has, in operation, the following features:
   the pressure in the reactive distillation column K1 is from 0.2 bar to 5 bar;
   the temperature at the top of the reactive distillation column K1 is from 25° C. to 125° C.;
   the temperature at the bottom of the reactive distillation column K1 is from 110° C. to 255° C.;
   the reactive distillation column K1 has from 10 to 40 theoretical plates;
   below the feedpoint, the reactive distillation column K1 has from 3 to 20 theoretical plates;

the reflux ratio in the reactive distillation column K1 is at least 0.20 g/g;

the pH in the reactive distillation column K1 in the region between feedpoint and bottom offtake including any side reactors present and the bottom is greater than 4.

14. Process according to claim 13, characterized in that the pressure in the reactive distillation column K1 is from 0.5 to 4 bar;

the temperature at the top of the reactive distillation column K1 is from 45 to 115° C.;

the temperature at the bottom of the reactive distillation column K1 is from 140 to 240° C.;

the reactive distillation column K1 has from 15 to 30 theoretical plates;

below the feedpoint, the reactive distillation column K1 has from 4 to 15 theoretical plates;

the pH in the reactive distillation column K1 in the region between feedpoint and bottom offtake is greater than 5.

15. Process according to claim 14, characterized in that the pressure in the reactive distillation column K1 is from 1 to 3 bar;

the temperature at the top of the reactive distillation column K1 is from 65 to 105° C.;

the temperature at the bottom of the reactive distillation column K1 is from 170 to 225° C.;

the reactive distillation column K1 has from 20 to 25 theoretical plates;

below the feedpoint, the reactive distillation column K1 has from 5 to 10 theoretical plates;

the pH in the reactive distillation column K1 in the region between feedpoint and bottom offtake is in the range from 7 to 14.

* * * * *